United States Patent [19]

Budai et al.

[11] Patent Number: 4,939,142
[45] Date of Patent: Jul. 3, 1990

[54] SUBSTITUTED STYRENE DERIVATIVES

[75] Inventors: Zoltán Budai; Lujza Petöcz; Tibor Mezei; Enikö Szirt née Kiszelly; Mária Szécsey née Hegedüs; Gábor Gigler; Klára Reiter née Esses; Aranka Lay née Kónya; Éva Furdyga; István Gertyán; István Gacsályi, all of Budapest, Hungary

[73] Assignee: EGIS Gyogyszergyar, Budapest, Hungary

[21] Appl. No.: 301,944

[22] Filed: Jan. 26, 1989

[51] Int. Cl.$^5$ .......................................... A61K 31/445
[52] U.S. Cl. ................................. 514/238.2; 544/398; 544/165; 546/232; 548/566; 564/256; 549/442; 514/255; 514/331; 514/358; 514/640; 514/464
[58] Field of Search ............... 544/398, 105; 546/232; 548/566; 564/256; 549/442; 514/238.2, 255, 331, 358, 640, 464

[56] References Cited

U.S. PATENT DOCUMENTS

| | | | |
|---|---|---|---|
| 4,077,999 | 3/1978 | Budai et al. | 564/256 |
| 4,395,413 | 6/1983 | Budai et al. | 564/256 |
| 4,727,074 | 2/1988 | Budai et al. | 564/256 |
| 4,803,286 | 2/1989 | Baldwin et al. | 564/256 |

FOREIGN PATENT DOCUMENTS 0168245  1/1986  European Pat. Off. ............ 564/256

*Primary Examiner*—James H. Reamer

[57] ABSTRACT

The new compounds of the general Formula I

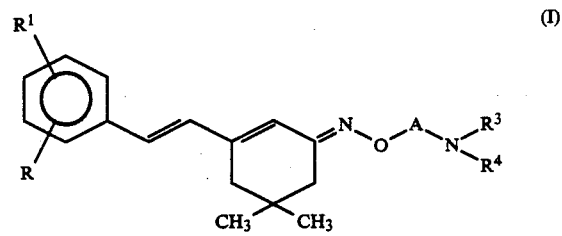

(wherein
A stands for a $C_{2-4}$ straight or branched chain alkylene group;
$R^1$ and $R^2$ may be same or different and each stands for hydrogen, halogen, lower alkyl or lower alkoxy; or
$R^1$ and $R^2$ together form a methylenedioxy group;
$R^3$ and $R^4$ may be the same or different and each stands for $C_{1-4}$alkyl or $C_{3-7}$cycloalkyl or
$R^3$ and $R^4$ together with the nitrogen atom, they are attached to, form a 4–7 membered ring which may contain as additional ring member an oxygen or sulfur atom or a further nitrogen atom and the latter nitrogen atom may optionally bear a $C_{1-3}$ alkyl or benzyl substituent)

and pharmaceutically acceptable acid addition salts and quaternary ammonium salts thereof possess valuable therapeutical properties and exert particularly useful transquillant-sedative, antidepressant, antiepileptic, antiparkinson, analgesic, local anaesthetic, gastric acid secretion inhibiting and/or antianginal effect.

The new compounds of the general Formula I may be prepared by methods known per se.

17 Claims, No Drawings

SUBSTITUTED STYRENE DERIVATIVES

This invention relates to new substituted styrene derivatives, a process for the preparation thereof and pharmaceutical compositions comprising the same.

According to an aspect of the present invention there are provided new substituted styrene derivatives of the general Formula I, and

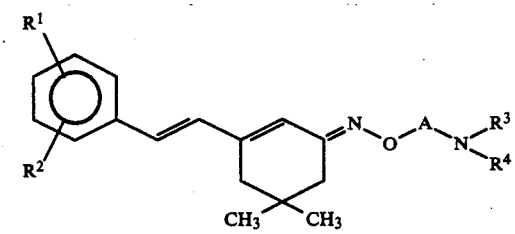

pharmaceutically acceptable acid addition salts and quaternary ammonium salts thereof
(wherein
A stands for a $C_{2-4}$ straight or branched chain alkylene group;
$R^1$ and $R^2$ may be same or different and each stands for hydrogen, halogen, lower alkyl or lower alkoxy; or
$R^1$ and $R^2$ together form a methylenedioxy group;
$R^3$ and $R^4$ may be the same or different and each stands for $C_{1-5}$ alkyl or $C_{3-6}$ cycloalkyl or
$R^3$ and $R^4$ together with the nitrogen atom, they are attached to, form a 4–7 membered ring which may contain as additional ring member an oxygen or sulfur atom or a further nitrogen atom and the latter nitrogen atom may optionally bear a $C_{1-3}$ alkyl or benzyl substituent).

The term "lower" designates groups having 1–4 carbon atoms. The term "alkyl" relates to straight or branched chain saturated aliphatic hydrocarbon groups (e.g. methyl, ethyl, n-propyl, isopropyl etc.). The term "alkoxy" relates to alkyl ether groups wherein the term "alkyl" corresponds to the above definition. The term "halogen" encompasses the chlorine, bromine, fluorine and iodine atoms and is preferably chlorine or bromine. The $-NR^3R^4$ heterocyclic ring may be preferably piperazinyl, N-methyl-piperazinyl, N-benzyl-piperazinyl, morpholino, pyrrolidino or piperidino.

"A" stands preferably for ethylene, trimethylene or 2-methyl-trimethylene.

$R^1$ and $R^2$ may be the same or different and each stands preferably for hydrogen, chlorine or methoxy.

$R^3$ and $R^4$ may be the same or different and each stands preferably for methyl or ethyl. The $-NR^3R^4$ group may preferably be dimethylamino, diethylamino, methyl-ethyl-amino, piperazino, N-benzyl-piperazino, N-methyl-piperazino, morpholino, pyrrolidino or piperidino.

The pharmaceutically acceptable salts of the compounds of the general Formula I may be salts formed with pharmaceutically acceptable inorganic or organic acids (e.g. hydrogen halides such as hydrochloric acid, hydrogen bromide; or sulfuric acid, nitric acid, phosphoric acid; maleic acid, fumaric acid, citric acid, tartaric acid, lactic acid, succinic acid, acetic acid, methanesulfonic acid, ethanesulfonic acid, propionic acid, malic acid etc.). The 2-(E)-butenedioates are particularly suitable salts.

The quaternary ammonium salts may be quaternary salts generally used in therapy.

The present invention encompasses all stereoisomers and optical isomers of the general Formula I and all mixtures thereof.

According to a further aspect of the present invention there is provided a process for the preparation of compounds of the general Formula I (wherein A, $R^1$, $R^2$, $R^3$ and $R^4$ are as stated above) and pharmaceutically acceptable acid addition salts and quaternary ammonium salts thereof which comprises reacting a stilbene derivative of the general Formula II

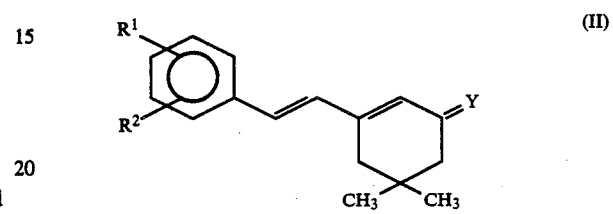

(wherein $R^1$ and $R^2$ are as stated above and Y represents oxygen, sulfur or a group of the Formula $=N-OH$) with an aminoalkyl derivative of the general Formula III

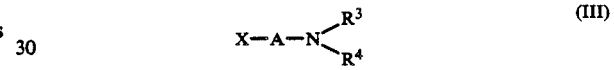

(wherein A, $R^3$ and $R^4$ are as stated above and X represents halogen or a group of the Formula $-O-NH_2$) in an inert solvent or solvent mixture in the presence of a basic condensing agent and, if desired, converting the compound of the general Formula I thus obtained into a pharmaceutically acceptable acid addition salt or quaternary ammonium salt or, if desired, setting free a compound of the general Formula I from a salt thereof.

The reaction of a stilbene derivative of the general Formula II and a compound of the general Formula III may be preferably carried out in an inert solvent or solvent mixture. As reaction medium e.g. an alcohol (e.g. ethanol), pyridine, an alkyl pyridine, triethyl amine, an aromatic hydrocarbon (e.g. benzene, toluene, xylene, cresol etc.), an ether (e.g. tetrahydrofurane, diisopropyl ether, dibutyl ether), dimethyl formamide, dimethyl acetamide or a mixture thereof (e.g. a mixture of dimethyl sulfoxide and water) may be used.

The reaction is accomplished in the presence of a basic condensing agent. The said condensing agent is selected depending on the definition of symbols X and Y. For this purpose e.g. an alkali metal (preferably sodium), an alkali amide (e.g. sodium amide), an alkali hydroxide (e.g. sodium or potassium hydroxide or a mixture thereof), or an organic base (e.g. pyridine, picoline or triethyl amine) may be used.

The reaction temperature varies between wide ranges. The reaction may be carried out at a temperature between about 25° C. and the boiling point of the reaction mixture. One may preferably work at a temperature interval between 50° C. and 130° C.

The compounds of the general Formula I thus obtained may be converted into pharmaceutically acceptable acid addition salts or quaternary ammonium salts. This reaction may be accomplished in a manner known per se by reacting the compound of the general Formula I in a suitable solvent with the corresponding acid. The quaternary ammonium compounds may also be prepared in a manner known per se by reacting the compound of the general Formula I with a suitable alkyl halide or methane sulfonic acid ester suitable for quaternarization.

The stilbene derivatives of the general Formula II used as starting material may be prepared by known methods by reacting isophorone with an aromatic aldehyde.

The starting materials of the general Formula III, wherein X stands for a $H_2N-O-$ group, may be prepared by the method disclosed in J. Pharm. Sci. 58, 138-140 (1969).

The starting materials of the general Formula III, wherein X stands for halogen, are known compounds and commercial products.

The compounds of the general Formula I possess valuable pharmacological properties. The compounds have a low toxicity (the $DL_{50}$ values are in the range of 1000-2000 mg/kg) and proved to be biologically active in various tests. The compounds of the general Formula I are particularly efficient in the hexobarbital narcosis potentiating, motility inhibiting, tetrabenazine ptosis antagonism, yohimbin toxicity, pentetrazol spasm inhibiting, maximal electroshock inhibiting, acetic acid "writhing" and nicotine spasm and lethality tests.

The compounds of the general Formula I exhibit particularly valuable tranquillant-sedative, antidepressant, antiepileptic, antiparkinson, analgesic, local anaesthetic, gastric acid secretion inhibiting and antianginal activity.

ACUTE TOXICITY

Male and female white mice (CFLP strain, 18-22 g) are used, 10 animals per dose. The test compounds are administered orally in a volume of 20 ml/kg. After administration the mice are observed for a period of 7 days. The animals are kept in plastic boxes, on wood litter, at room temperature. The animals receive standard mouse fodder and tap water ad libitum. The toxicity data are determined by means of the method of Litchfield and Wilcoxon [J. L. Litchfield and F. W. Wilcoxon: J. Pharmacol. Exp. Ther. 96, 99 (1949)]. The $DL_{50}$ data thus obtained are in the range of 1000-2000 mg/kg.

HEXOBARBITAL NARCOSIS POTENTIATING EFFECT

The test is carried out on white mice. Groups consisting of six mice are used for each dose and test compound. The test compound is administered orally and an hour after this treatment narcosis is induced by means of a 40 mg/kg i.v. dose of hexobarbital. The control group receives carrier instead of the test compound.

EVALUATION

Those mice are considered to be having a positive reaction which show a narcosis time at least 2.5 times longer than that of the control group. The $ED_{50}$ values thus transformed are calculated. The results are summarized in Table I.

TABLE I

| Hexobarbital narcosis potentiating effect | | | |
|---|---|---|---|
| Test compound Example No. | $LD_{50}$ mg/kg | $ED_{50}$ | Therapeutical index $LD_{50}/ED_{50}$ |
| 16 | 1850 | 40 | 46.0 |

TABLE I-continued

| Hexobarbital narcosis potentiating effect | | | |
|---|---|---|---|
| Test compound Example No. | $LD_{50}$ mg/kg | $ED_{50}$ | Therapeutical index $LD_{50}/ED_{50}$ |
| 17 | 1600 | 13 | 123.0 |
| 15 | 2000 | 25 | 80.0 |
| 13 | 1800 | 9 | 200.0 |
| 12 | 1000 | 100 | 20.0 |
| 11 | 2000 | 140 | 14.3 |
| 8 | 2000 | 180 | 11.1 |
| 30 | >2000 | 21.5 | >93.0 |
| 29 | >2000 | 21.5 | >93.0 |
| Meprobamate | 1100 | 260 | 4.2 |
| Chlordiazepoxid | 620 | 10 | 62.0 |

MOTILITY INHIBITING ON MICE

The test is accomplished according to the method of Borsy et al. in a 10-channel Dews system equipment, whereby 3 mice are used per channel. The test compound or the carrier, respectively, is administered orally, and one hour after the said treatment the animals are placed into the apparatus and the number of the interruptions of infrared radiation is registered for 30 minutes.

EVALUATION

The results are summarized in Table II and documented by means of suitable statistics for each experiment.

TABLE II

| Motility inhibition on mice | | | |
|---|---|---|---|
| Test compound No. of Example | $LD_{50}$ mg/kg | $ED_{50}$ mg/kg | Therapeutical index |
| 2 | 2000 | 190 | 10.5 |
| 1 | 1300 | 60 | 22.0 |
| 3 | 1000 | 58 | 17.0 |
| 16 | 1850 | 150 | 12.3 |
| 5 | 2000 | 120 | 17.0 |
| 13 | 1800 | 100 | 18.0 |
| 10 | 1000 | 60 | 16.7 |
| 8 | 2000 | 170 | 11.8 |
| 25 | 1300 | about 200 | 6.5 |
| 26 | >1000 | about 200 | >5.0 |
| 30 | >2000 | about 200 | >10.0 |
| 29 | >2000 | about 200 | >10.0 |
| Meprobamate | 1100 | 270 | 4.1 |

[J. Borsy, E. Csanyi, I. Lazar: Arch. Int. Pharmacodyn. 124, 1 (1960)].

TETRABENAZIN PTOSIS ANTAGONISM

Method

The test is carried out by the method of Hoffmeister et al. adapted to mice. Groups consisting of 10-20 animals are treated orally with each dose of the test compound. The control group is treated orally with the carrier. Thirty minutes later a 50 mg/kg i.p. tetrabenazine dose is administered, whereupon after 30, 60, 90 and 120 minutes the animals with closed eye-lids are counted in each group.

EVALUATION

On the basis of all measurements an average ptosis is calculated for each group and expressed as the percentile deviation (inhibition) from the control group. On the basis of the data thus obtained $ED_{50}$ values are calculated. The results are summarized in Table III.

TABLE III

| Test compound No. of Example | LD50 mg/kg | ED50 mg/kg | Therapeutical index |
|---|---|---|---|
| 18 | 2000 | 40.0 | 50.0 |
| 20 | 2000 | 8.5 | 235.3 |
| Amitriptylin | 225 | 12.0 | 18.7 |

[Hoffmeister, F., Wuttke, W., and Kroneberg, G.: Arzneim.-Forsch. (Drug. Res.) 19, 846 (1969)].

YOHIMBIN TOXICITY ON MICE

Method

The test is carried out according to the method of Quinton. Groups consisting of 10 mice are used for each dose. The animal groups are treated with the suitable doses of the test compounds while the control group is treated with a carrier. An hour after the treatment a sublethal dose of yohimbin is administered intraperitoneally in a volume of 20 ml/kg. The perished animals are counted after 1 and 24 hours. The results are summarized in Table IV.

TABLE IV

| | Yohimbin toxicity | | |
|---|---|---|---|
| Test compound No. of Example | LD50 mg/kg | ED50 mg/kg | Therapeutical index |
| 11 | 2000 | 40 | 50 |
| 10 | 1000 | 40 | 25 |
| 9 | 2000 | 50 | 40 |
| 8 | 2000 | 35 | 57.1 |
| 7 | 2000 | 60 | 33.3 |
| Viloxazin | 440 | 20 | 22 |
| Imipramin | 320 | 21 | 15.2 |
| Amitriptylin | 225 | 12.5 | 18 |

[Quinton, R. M.: Brit. J. Pharmacol. 21, 51 (1963)].

INHIBITION OF PENTETRAZOL SPASM ON MICE

Method

The modified method of Benziger and Hane is used on white mice. Groups consisting of 6 animals are used for each dose. The tonus extensor spasms of the posterior extremities induced by a 125 mg/kg i.p. dose of pentetrazole are registered. The test compounds are administered orally one hour before the treatment with pentetrazole; in the control group the animals obtain the carrier orally at the same points of time. The results are disclosed in Table V.

TABLE V

| Inhibition of pentetrazole spasm on mice | | | |
|---|---|---|---|
| Test compound No. of Example | LD50 mg/kg | ED50 mg/kg | Therapeutical index |
| 2 | 2000 | 140 | 14.3 |
| 1 | 1300 | 56 | 23.2 |
| 3 | 1000 | 68 | 14.7 |
| 16 | 1850 | 185 | 10.0 |
| 17 | 1600 | 148 | 10.8 |
| 18 | 2000 | 190 | 10.5 |
| 4 | 2000 | 180 | 11.1 |
| 5 | 2000 | 125 | 16.0 |
| 15 | 2000 | 120 | 16.6 |
| 14 | 2000 | 70 | 28.5 |
| 12 | 1000 | 23 | 43.5 |
| 11 | 2000 | 78 | 25.6 |
| 9 | 2000 | 160 | 12.5 |
| 8 | 2000 | 58 | 34.5 |
| 7 | 2000 | 80 | 25.0 |
| 23 | 1000 | 58.0 | 17.2 |
| 25 | 1300 | 15.5 | 83.9 |
| 33 | >1000 | 63.0 | >15.9 |

TABLE V-continued

| Inhibition of pentetrazole spasm on mice | | | |
|---|---|---|---|
| Test compound No. of Example | LD50 mg/kg | ED50 mg/kg | Therapeutical index |
| 24 | >1000 | 110.0 | >9.1 |
| 34 | >2000 | 180.0 | >11.0 |
| Trimethadion | 2050 | 490 | 4.3 |

[Bensiger, R., Hane, D.: Arch. Int. Parmacodyn. 167, 245 (1967)].

MAXIMAL INHIBITION OF ELECTROSHOCK ON WHITE MICE

Method

The test is carried out on white mice weighing 20–25 g. The animals receive an electric shock through corneal electrodes (50 Hz; 45 mA, 0.4 sec.). A total inhibition of the tonus extensor spasms of the posterior extremities is regarded as the criterium of anticonvulsive effect. The test compound and the carrier, respectively, are administered orally an hour before the electric shock. The results are summarized in Table VI.

TABLE VI

| Inhibition of maximal electroshock on mice | | | |
|---|---|---|---|
| Test compound No. of Example | LD50 mg/kg | ED50 mg/kg | Therapeutical index |
| 1 | 1300 | 110 | 11.8 |
| 3 | 1000 | 88 | 11.4 |
| 13 | 1800 | 64 | 28.1 |
| Trimethadion | 2050 | 400 | 5.1 |

[Swinyard et al.: J. Pharmacol. Exp. Ther. 106, 319 (1952)].

ACETIC ACID "WRITHING TEST" ON MICE

Method

The test is carried out according to the method of Newbould on white mice except that the amount of intraperitoneally administered acetic acid is modified. More reliable responses are obtained by using a concentration of 0.75%, a dose of 20 mg/kg and a volume of 20 ml/kg. In the period between the 5th and 10th minutes following the administration of acetic acid the number of the characteristic "writhing" responses is counted for each animal and the "total writhing number" (within 5 minutes) is expressed as the percentage of the value obtained for the control animals. The mice are treated with the test compound and the carrier, respectively, orally 1 hour before the administration of acetic acid. 12 animals are used per dose. The results are disclosed in Table VII.

TABLE VII

| Acetic acid "writhing test" on mice | | | |
|---|---|---|---|
| Test compound No. of Example | LD50 mg/kg | ED50 mg/kg | Therapeutical index |
| 1 | 1300 | 160 | 8.1 |
| 5 | 2000 | 155 | 12.9 |
| 12 | 1000 | 50 | 20.0 |
| 10 | 1000 | 153 | 6.5 |
| 8 | 2000 | 178 | 11.2 |
| 25 | 1300 | about 200 | 65 |
| 29 | >2000 | about 160 | >12.5 |
| 34 | >2000 | about 200 | >10.0 |
| Paracetamol | 510 | 180 | 2.8 |

[Newbould, B. D.: Brit. J. Pharmacol. 35, 487 (1969)].

INHIBITION OF NICOTINE SPASM AND LETHALITY ON MICE

Method

The test is carried out according to the method of Stone. The test compounds and the carrier, respectively, are administered orally; an hour later the animals receive a 1.4 mg/kg i.v. dose of nicotine and the spasms and lethality are registered within an hour for the treated and control groups. The results are summarized in Table VIII.

TABLE VIII

| Test compound No. of Example | LD$_{50}$ mg/kg | ED$_{50}$ mg/kg | Therapeutical index |
| --- | --- | --- | --- |
| 2 | 2000 | 78 | 25.6 |
| 1 | 1300 | 12 | 108.0 |
| 3 | 1000 | 33 | 30.3 |
| 16 | 1850 | 70 | 26.4 |
| 17 | 1600 | 40 | 40.0 |
| 18 | 2000 | 88 | 22.7 |
| 15 | 2000 | 70 | 28.6 |
| 8 | 2000 | 35 | 57.1 |
| 7 | 2000 | 80 | 25 |
| Trihexyphenidyl | 365 | 20 | 18.3 |

[Stone, C. C., Mecklenburg, K. L., Torchiana, M. L.: Arch. Int. Pharmacodyn. 117, 419 (1958)].

ANTIANGINAL EFFECT ON RATS

Method

The test is carried out on male rats weighing 180-220 g. The animals are narcotized with the aid of chloralose urethane (70-700 mg/kg i.p.). ECG is registered by means of needle electrodes in standard II output. Antianginal effect is tested according to the method of Nieschultz. Experimental coronary insufficiency is induced by administering vasopressine (1 IU/kg i.v.) on 10–12 animals for each dose. The magnitude of the T-wave before and after the administration of vasopressine is measured in the treated and control groups. The results are summarized in Table IX.

TABLE IX

| Test compound Example No. | Dose mg/kg | Inhibition % |
| --- | --- | --- |
| 28 | 2 | −31 |
| 30 | 2 | −45 |
| 33 | 2 | −47.1 |
| 20 | 2 | −54.4 |
| Prenylamine | 2 | −32.0 |

INHIBITION OF ULCUS SECRETION ON RATS

Method

The test is carried out according to the method of Nakamura on rats (Wistar strain) weighing 150-230 g and fasted for 48 hours. Each animal group consists of 4 male and 4 female rats. On the day of the experiment the pylorus of the animals is bound and the corresponding dose of the test compound is administered orally immidiately after operation. The animals are killed with ether 5 hours after the operation, their stomach is removed, cut along the large curve and placed on plastic plates. The results are summarized in Table X.

TABLE X

| Test compound Example No. | LD$_{50}$ mg/kg | ED$_{50}$ mg/kg | Therapeutical index |
| --- | --- | --- | --- |
| 26 | above 1000 | about 50 | above 20 |
| 30 | above 2000 | about 150 | above 13.3 |
| 29 | above 2000 | about 200 | above 10.0 |
| 34 | above 2000 | about 100 | above 20.0 |
| Trithiozine | above 200 | about 240 | above 8.3 |

The therapeutical index data disclosed in the above Tables are calculated by means of the following equation:

$$\text{Therapeutical index} = \frac{LD_{50}}{ED_{50}}$$

According to a further aspect of the present invention there are provided pharmaceutical compositions comprising as active ingredient at least one compound of the general Formula I or a pharmaceutically acceptable acid addition salt or a quaternary ammonium salt thereof. The pharmaceutical compositions of the present invention are suitable for oral, rectal or parenteral administration. The active ingredient may be finished in solid (e.g. tablet, pill, coated, pill, dragée, capsule, suppository), semi-solid (e.g. ointment) or liquid (e.g. solution, emulsion, suspension) form. The pharmaceutical compositions contain suitable conventional organic or inorganic solid or liquid carriers (e.g. starch, talc, magnesium stearate, calcium carbonate, water, polyalkylene glycols etc.). The compositions may also contain suitable conventional auxiliary agents (e.g. preserving, stabilizing, suspending, emulsifying, wetting agents, disintegrants, buffers, salts for modifying the osmotic pressure etc.). The compositions may also contain in addition to the compounds of the general Formula I other therapeutically valuable compounds.

The pharmaceutical compositions of the present invention may be prepared by methods of the pharmaceutical industry known per se by admixing a compound of the general Formula I or a pharmaceutically acceptable acid addition salt or quaternary ammonium salt thereof with suitable inert solid or liquid pharmaceutical carriers and bringing the mixture to a galenic form.

According to a further aspect of the present invention there is provided the use of compounds of the general Formula I or pharmaceutically acceptable acid addition salts or quaternary ammonium salts thereof for the preparation of pharmaceutical compositions having tranquillant-sedative, antidepressant, antiepileptic, antiparkinson, analgesic, local anaesthetic, gastric acid secretion inhibiting and/or antianginal effect.

If is preferred to finish the compounds of the general Formula I to dosage forms having an active ingredient content of 0.5-500 mg.

According to a still further aspect of the present invention there is provided a method of tranquillantsedative, antidepressant, antiepileptic, antiparkinson, analgesic, local anaesthetic, gastric acid secretion inhibitory and/or antianginal treatment which comprises administering to the patient in an effective amount a compound of the general Formula I or a pharmaceutically acceptable acid addition salt or quaternary ammonium salt thereof.

Further details of the present invention are to be found in the following Examples without limiting the scope of protection to the said Examples.

EXAMPLE 1

5,5-Dimethyl-3-(E)-phenyl-vinyl-1-(E)-(3'-dimethylamino-propoxyimino)-2-cyclohexene To a suspension of 2.4 g (0.1 mole) of sodium hydride and 50 ml of anhydrous xylene at 60° C. a solution of 22.9 g (0.1 mole) of 5,5-dimethyl-3-(E)-phenyl-vinyl-2-cyclohexene-1-one-(E)-oxime in 150 ml of anhydrous xylene is added under constant stirring. The reaction mixture is stirred at 60° C. for 2 hours whereupon a solution of 13.3 g (0.11 mole) of 1-dimethylamino-3-chloro-propane and 20 ml of xylene is added under constant stirring. The reaction mixture is stirred for a further period of 6 hours at 130° C., then cooled to 30° C. The mixture is washed with 100 ml of water and thereafter extracted with an aqueous solution of 15 g (0.1 mole) of tartaric acid or a mixture of 11.0 g (0.11 mole) of 36.5% aqueous hydrochloric acid and 50 ml of water. The aqueous solution is cooled to 0°-5° C. whereupon it is made alkaline to a pH value of 10, with a concentrated ammonium hydroxide solution. The precipitated oily base is extracted with dichloro ethane. The solvent is evaporated and the residue fractionated in vacuo. Thus 23.3 g of the desired compound are obtained, yield 71.5%. B. p.: 178°-180° C./25 Pa.

2-(E)-Butenedioate (1/1)

22.8 g of (0.07 mole) of the above base are dissolved in 200 ml of acetone, whereupon 8.1 g (0.07 mole) of fumaric acid are added under vigorous stirring. After dissolving of the fumaric acid yellow fluffy crystals precipitate within some minutes. The mixture is allowed to crystallize at 0° C. for 3 hours, the precipitated crystals are filtered and dried. Thus 29.9 g of the desired salt are obtained, yield 96.4%, m. p.: 152°-154° C.

Analysis for the Formula $C_{25}H_{34}N_2O_5$ (442.5): Calculated: C %=67.85; H %=7.74; N %=6.33; found: C %=67.93; H %=7.97; N %=6.19.

U.V.: $\lambda_{max}1=320$ nm ($\epsilon=48363$) and $\lambda_{max}2=328$ nm ($\epsilon=38973$).

EXAMPLE 2

5,5-Dimethyl-3-(E)-phenyl-vinyl-1-(E)-(4'-methyl-1'-piperazinyl-propoxyimino)-2-cyclohexene One proceeds in an analogous manner to Example 1 except that 1-dimethylamino-3-chloro-propane is replaced by 19.4 g of (0.11 mole) of 1-(4'-methyl-piperazinyl)-3-chloro-propane. Thus 32.2 g of the desired compound are obtained, yield 87.0%, viscous oil.

The 2-(E)-butenedioate (½) salt melts at 218°-220° C.

Analysis for the Formula $C_{32}H_{43}N_3O_9$ (613.7): Calculated: C %=62.63; H %=7.06; N %=6.85; found: C %=63.07; H %=7.12; N %=6.87.

U.V.: $\lambda_{max}=318$ nm ($\epsilon=48388$).

EXAMPLE 3

5,5-Dimethyl-3-(E)-phenyl-vinyl-1-(E)-(2'-dimethylamino-ethoxyimino)-2-cyclohexene To a suspension of 2.4 g (0.1 mole) of sodium hydride in 100 ml of anhydrous benzene at 50° C. a solution of 22.9 g (0.1 mole) of 5,5-dimethyl-3-(E)-phenyl-vinyl-2-cyclohexene-1-one-(E)-oxime and 50 ml of anhydrous dimethyl formamide is added under constant stirring. The mixture is stirred for 10 minutes whereupon at 60° C. a mixture of 11.8 g (0.11 mole) of 1-dimethylamino-2-chloro-ethane and 20 ml of anhydrous benzene is added. The reaction mixture is stirred for 4 hours under boiling, then cooled, whereupon it is extracted with a solution of 16.5 g (0.11 mole) of tartaric acid and 100 ml of water. The aqueous phase is cooled to 0°-5° C., made alkaline with ammonium hydroxide to pH 10, extracted with dichloro ethane and the solvent is evaporated. Thus 29.8 g the desired compound are obtained, yield 95.3%.

The 2-(E)-butenedioate salt (1/1) melts at 216°-219° C.

Analysis for the Formula $C_{24}H_{32}N_2O_5$ (428.5): Calculated: C %=67.26; H %=7.53; N %=6.54; found: C %=67.73; H %=7.67; N %=6.64.

U.V.: $\lambda_{max}=318$ nm ($\epsilon=48475$).

EXAMPLE 4

5,5-Dimethyl-3-(E)-[(4'-chloro-phenyl)-vinyl]-1-(E)-(4''-methyl-1''-piperazinyl-propoxyimino)-2-cyclohexene One proceeds in an analogous manner to Example 2 except that 5,5-dimethyl-3-(E)-phenyl-vinyl-2-cyclohexene-1-one-(E)-oxime is replaced by 26.4 g (0.1 mole) of 5,5-dimethyl-3-(E)-[(4'-chloro-phenyl)-vinyl]-2-cyclohexene-1-one-(E)-oxime. Yield 48.1 g (93.2%).

The 2-(E)-butenedioate salt (½) melts at 218°-220° C.

Analysis for the Formula $C_{32}H_{42}ClN_3O_9$; Calculated: C %=59.59; H %=6.53; Cl %=5.47; N %=6.48; found: C %=59.61; H %=6.62; Cl %=5.50; N %=6.42.

U.V.: $\lambda_{max}=324$ nm ($\epsilon=500.99$).

EXAMPLE 5

5,5-Dimethyl-3-(E)-[(4'-chloro-phenyl)-vinyl]-1-(E)-(3''-dimethylamino-propoxyimino)-2-cyclohexene To a sodium ethylate solution prepared from 9.2 g (0.4 mole) of sodium and 200 ml of anhydrous ethanol at room temperature 26.4 g (0.1 mole) of 5,5-dimethyl-3-(E)-[(4'-chloro-phenyl)-vinyl]-2-cyclohexene-1-one-(E)-oxime and 23.7 g (0.15 mole) of 1-dimethylamino-3-chloro-propane-hydrochloride are added. The reaction mixture is heated to boiling for 4 hours, whereupon it is cooled to room temperature, the precipitated sodium chloride is filtered off and the filtrate is evaporated in vacuo. The residue is admixed with 100 ml of water, extracted with chloroform and evaporated. Thus 128.8 g of the desired compound are obtained, yield 89.2%.

The 2-(E)-butenedioate salt (1/1) melts at 178°-180° C.

Analysis for the Formula $C_{25}H_{33}ClN_2O_5$ (477.0): Calculated: C %=62.96; H %=6.97; Cl %=7.43; N %=5.87; found: C %=63.05; H %=7.03; Cl %=7.47; N %=5.84.

U.V.: $\lambda_{max}1=229$ nm ($\epsilon=13517$), $\lambda_{max}2=322$ nm ($\epsilon=53312$).

EXAMPLE 6

5,5-Dimethyl-3-(E)-[(3',4'-dichloro-phenyl)-vinyl]-1-(E)-(3''-dimethylamino-propoxyimino)-2-cyclohexene One proceeds in an analogous manner to Example 1 except that sodium hydride is replaced by 3.9 g (0.1 mole) of sodium amide and in place of 5,5-dimethyl-3-(E)-phenyl-vinyl-2-cyclohexene-1-one-(E)-oxime 29.8 g (0.1 mole) of 5,5-dimethyl-3-(E)-[(3',4'-dichloro-phenyl)-vinyl]-2-cyclohexene-1-one-(E)-oxime are used. Thus 34.9 g of the desired compound are obtained, yield 88.3%.

The 2-(E)-butenedioate salt (1/1) melts at 164°–166° C.

Analysis for the Formula $C_{25}H_{32}Cl_2N_2O_5$ (511.4): Calculated: C %=58.71; H %=6.31; Cl %=13.86; N %=5.48; found: C %=58.92; H %=6.51; Cl %=13.83; N %=5.41.

U.V.: $\lambda_{max}1=322$ nm ($\epsilon=25500$) and $\lambda_{max}2=240$ nm ($\epsilon=6923$).

EXAMPLE 7

5,5-Dimethyl-3-[(2',6'-dichloro-phenyl)-vinyl]-1-(E)-(3''-dimethylamino-propoxyimino)-2-cyclohexene One proceeds in an analogous manner to Example 1 except that sodium hydride is replaced by 5.5 g (0.1 mole) of potassium amide and as oxime 29.8 g (0.1 mole) of 5,5-dimethyl-3-(E)-[(2',6'-dichloro-phenyl)-vinyl]-2-cyclohexene-1-one-(E)-oxime are used. Thus 37.1 g of the desired compound are obtained, yield 93.8%.

The 2-(E)-butenedioate salt (1/1) melts at 135°–137° C.

Analysis for the Formula $C_{25}H_{32}Cl_2N_2O_5$ (511.4): Calculated: C %=58.71; H %=6.31; Cl %=13.86; N %=5.48; found: C %=58.87; H %=6.42; Cl %=13.78; N %=5.40.

U.V.: $\lambda_{max}=308$ nm ($\epsilon=34345$).

EXAMPLE 8

5,5-Dimethyl-3-(E)-[(3'-chloro-phenyl)-vinyl]-1-(E)-(3''-dimethylamino-propoxyimino)-2-cyclohexene A mixture of 24.8 g (0.1 mole) of 5,5-dimethyl-3-(E)-[(3'-chloro-phenyl)-vinyl]-2-cyclohexene-1-one, 19.1 g (0.1 mole) of 1-dimethylamino-3-propoxy-amine-hydrochloride, 200 ml of anhydrous ethanol and 75 ml of pyridine is heated to boiling for 2 hours whereupon the solvent is removed in vacuo. The residue is made alkaline with a sodium hydroxide solution to pH 10 whereupon the base is extracted with dichloro ethane. Thus 33.0 g of the desired compound are obtained, yield 91.4%.

The 2-(E)-butanedioate salt (1/1) melts at 150°–153° C.

Analysis for the Formula $C_{25}H_{33}ClN_2O_5$ (477.0): Calculated: C %=62.95; H %=6.97; Cl %=7.43; N %=5.87; found: C %=62.87; H %=7.10; Cl %=7.34; N %=5.80;

U.V.: $\lambda_{max}=322$ nm ($\epsilon=46681$).

EXAMPLE 9

5,5-Dimethyl-3-(E)-[(2'-chloro-phenyl)-vinyl]-1-(E)-(3''-dimethylamino-propoxyimino)-2-cyclohexene To a solution of 40 g (1.0 mole) of sodium hydroxide and 11.2 g (0.2 mole) of potassium hydroxide in 50 ml of water 20 ml of dimethyl sulfoxide, 26.5 g (0.1 mole) of 5,5-dimethyl-3-(E)-[(2'-chloro-phenyl)-vinyl]-2-cyclohexene-1-one-(E)-oxime and 13.4 g (0.11 mole) of 1-dimethylamino-3-chloro-propane are added, whereupon the mixture is stirred for a further period of 4 hours at 50°–60° C. under vigorous stirring. The mixture is cooled, diluted with water, the base is extracted with benzene and the solvent is removed in vacuo. Thus 31.2 g of the desired compound are obtained, yield 86.7%.

The 2-(E)-butenedioate (1/1) salt melts at 136°–138° C.

Analysis for the Formula $C_{25}H_{32}ClN_2O_5$ (476.0): Calculated: C %=63.08; H %=6.78; Cl %=7.45; N %=5.88; found: C %=62.94; H %=6.82; Cl %=7.35; N %=5.82.

U.V.: $\lambda_{max}=322$ nm ($\epsilon=41356$).

EXAMPLE 10

5,5-Dimethyl-3-(E)-[(3',4'-dimethoxy-phenyl)-vinyl]-1-(E)-(3''-dimethylamino-propoxyimino)-2-cyclohexene One proceeds in an analogous manner to Example 9 except that as oxime 28.9 g (0.1 mole) of 5,5-dimethyl-3-(E)-[(3',4'-dimethoxy-phenyl)-vinyl]-2-cyclohexene-1-one-(E)-oxime are used. Thus 34.1 g of the desired compound are obtained, yield 88.3%.

The 2-(E)-butenedioate salt (1/1) melts at 135°–138° C.

Analysis for the Formula $C_{27}H_{38}N_2O_7$ (502.6): Calculated: C %=64.52; H %=7.62; N %=5.58; found: C %=64.79; H %=7.66; N %=5.62.

U.V.: $\lambda_{max}1=839.8$ nm ($\epsilon=42215$), $\lambda_{max}2=253.6$ nm ($\epsilon=12759$).

EXAMPLE 11

5,5-Dimethyl-3-(E)-[(4'-methoxy-phenyl)-vinyl]-1-(E)-(3''-dimethylamino-propoxyimino)-2-cyclohexene One proceeds according to Example 9 except that 25.9 g (0.1 mole) of 5,5-dimethyl-3-(E)-[(4'-methoxy-phenyl)-vinyl]-2-cyclohexene-1-one-(E)-oxime are used as oxime. Thus 32.9 g of the desired compound are obtained, yield 92.3%.

The 2-(E)-butenedioate salt (1/1) melts at 163°–165° C.

Analysis for the Formula $C_{26}H_{36}N_2O_6$ (472.6): Calculated: C %=66.08; H %=7.68; N %=5.93; found: C %=66.15; H %=7.76; N %=5.89.

U.V.: $\lambda_{max}=$ nm ($\epsilon=45532$).

EXAMPLE 12

5,5-Dimethyl-3-(E)-phenyl-vinyl)-1-(E)-2'-[bis-(2''-methyl-ethyl)-amino-ethoxyimino]-2-cyclohexene To a suspension of 2.4 g (0.1 mole) of sodium hydride and 100 ml of anhydrous benzene at 50° C. a solution of 22.9 g (0.1 mole) of 5,5-dimethyl-3-(E)-phenyl-vinyl-2-cyclohexene-1-one-(E)-oxime in 50 ml of anhydrous dimethyl formamide is added dropwise under constant stirring. The gas evolution having been completed 15.7 g (0.1 mole) of 1-bromo-3-chloro-propane are added at 60° C., whereupon the suspension is heated to boiling for 2 hours. After cooling the reaction mixture is washed with water and evaporated in vacuo. Thus 28.5 g of 5,5-dimethyl-3-(E)-phenyl-vinyl-1-(E)-(3'-chloro-propoxyimino)-2-cyclohexene are obtained (yield 93.2%). To this product 250 ml of anhydrous ethanol and 20.2 g (0.2 mole) of diisopropyl amine are added. The reaction mixture is heated to boiling for 10 hours. The brown solution is evaporated in vacuo, whereupon 200 ml of water and 20 ml of a concentrated ammonium hydroxide solution are added. The mixture is extracted twice with 100 ml of benzene each, dried and evaporated in vacuo. Thus 29.9 g of the desired compound are obtained, yield 81.3%.

The 2-(E)-butenedioate salt (1/1) melts at 123°–125° C.

Analysis for the Formula $C_{28}H_{40}N_2O_5$ (484.6): Calculated: C %=69.39; H %=8.32; N %=5.78; found: C %=69.55; H %=8.25; N %=5.75.

U.V.: $\lambda_{max}=320$ nm ($\epsilon=53413$).

EXAMPLE 13

D,L-5,5-Dimethyl-3-(E)-phenyl-vinyl-1-(E)-(3'-dimethylamino-2'-methyl-propoxyimino)-2-cyclohexene One proceeds in an analogous manner to Example 3 except that 1-dimethylamino-3-chloro-propane is replaced by 14.9 g (0.11 mole) of 1-dimethylamino-2-methyl-3-chloro-propane. Thus 29.0 g of the desired compound are obtained, yield 85.2%.

The 2-(E)-butenedioate salt (1/1) melts at 173°–175° C.

Analysis for the Formula $C_{26}H_{36}N_2O_5$ (456.6): Calculated: C %=69.39; H %=7.95; N %=6.15; found: C %=69.12; H %=8.04; N %=6.04.

U.V.: $\lambda_{max}1$=227 nm ($\epsilon$=13848), $\lambda_{max}2$=318 nm ($\epsilon$=52267).

EXAMPLE 14

5,5-Dimethyl-3-(E)-[(4'-chloro-phenyl)-vinyl]-1-(E)-2'''-[bis-(2''-methyl-ethyl)-amino-ethoxyimino]-2-cyclohexene One proceeds in an analogous manner to Example 3 except that 26.4 g (0.1 mole) of 5,5-dimethyl-3-(E)-[(4'-chloro-phenyl)-vinyl]-2-cyclohexene-1-one-(E)-oxime are reacted with 18.0 g (0.11 mole) of 1-diisopropylamino-2-chloro-ethane. Thus 34.2 g of the desired compound are obtained, yield 84.9%.

The 2-(E)-butenedioate salt (1/1) melts at 150°–151° C.

Analysis for the Formula $C_{28}H_{39}ClN_2O_5$ (519.1): Calculated: C %=64.78; H %=7.57; Cl %=6.83; N %=5.39; found: C %=64.37; H %=7.44; Cl %=6.66; N %=5.32.

U.V.: $\lambda_{max}$=325 nm ($\epsilon$=53228).

EXAMPLE 15

5,5-Dimethyl-3-(E)-[(4'-chloro-phenyl)-vinyl]-1-(E)-(2''-dimethylamino-ethoxyimino)-cyclohexene One proceeds in an analogous manner to Example 5 except that 1-dimethylamino-3-chloro-propane is replaced by 11.8 g (0.11 mole) of 1-dimethylamino-2-chloro-ethane. Thus 29.5 g of the desired compound are obtained, yield 84.9%.

The 2-(E)-butenedioate salt (1/1) melts at 176°–178° C.

Analysis for the Formula $C_{24}H_{31}ClN_2O_5$ (463.0): Calculated: C %=62.26; H %=6.74; Cl %=7.65; N %=6.05; found: C %=62.26; H %=6.38; Cl %=7.57; N %=5.99.

U.V.: $\lambda_{max}$=325 nm ($\epsilon$=55759).

EXAMPLE 16

5,5-Dimethyl-3-(E)-phenyl-vinyl-1-(E)-(2'-N-piperidyl-ethyl)-oxyimino-2-cyclohexene One proceeds in an analogous manner to Example 3 except that 2-dimethylamino-1-chloro-ethane is replaced by 16.2 g (0.11 mole) N-piperidyl-2-chloro-ethane. Thus 26.2 g of the desired compound are obtained, yield 74.3%.

The 2-(E)-butenedioate salt (1/1) melts at 157°–159° C.

Analysis for the Formula $C_{27}H_{36}N_2O_5$ (468.6): Calculated: C %=69.19; H %=7.75; N %=5.98; found: C %=68.92; H %=7.82; N %=5.95.

U.V.: $\lambda_{max}$=318 nm ($\epsilon$=47116).

EXAMPLE 17

5,5-Dimethyl-3-(E)-phenyl-vinyl-1-(E)-(N-morpholino-ethoxyimino)-2-cyclohexene

One proceeds in an analogous manner to Example 3 except that 1-dimethylamino-2-chloro-ethane is replaced by 16.5 g (0.11 mole) of 1-morpholino-2-chloro-ethane. Thus 30.0 g of the desired compound are obtained, yield 87.8%.

The 2-(E)-butenedioate salt (1/1) melts at 154°–155° C.

Analysis for the Formula $C_{25}H_{34}N_2O_6$ (458.5): Calculated: C %=65.48; H %=7.47; N %=6.11; found: C %=65.73; H %=7.56; N %=6.05.

U.V.: $\lambda_{max}$=318 nm ($\epsilon$=42172).

EXAMPLE 18

D,L-5,5-Dimethyl-3-(E)-[(4'-chloro-phenyl)-vinyl]-1-(E)-(3''-dimethylamino-2''-methyl-propoxyimino)-2-cyclohexene One proceeds in an analogous manner to Example 3 except that 26.4 g of 5,5-dimethyl-3-(E)-[(4'-chloro-phenyl)-vinyl]-2-cyclohexene-1-one-(E)-oxime and 14.91 g (0.11 mole) of 1-dimethylamino-2-methyl-3-chloro-propane are used as starting material. Thus 34.2 g of the desired compound are obtained, yield 91.3%, m. p.: 65°–67° C.

The 2-(E)-butenedioate salt (1/1) melts at 180°–183° C.

Analysis for the Formula $C_{26}H_{35}ClN_2O_5$ (491.0): Calculated: C %=63.59; H %=7.19; Cl %=7.22; N %=5.71; found: C %=63.53; H %=7.23; Cl %=7.19; N %=5.43.

U.V.: $\lambda_{max}$=238 nm ($\epsilon$=13867).

EXAMPLE 19

5,5-Dimethyl-3-(E)-[(4'-chloro-phenyl)-vinyl]-1-(E)-3''-[bis-(2'-methyl-ethyl)-amino-propoxyimino]-2-cyclohexene One proceeds in an analogous manner to Example 12 except that 26.4 g (0.1 mole) of 5,5-dimethyl-3-(E)-[(4'-chloro-phenyl)-vinyl]-2-cyclohexene-1-one-(E)-oxime are used as oxime component. Thus 34.1 g of the desired compound are obtained, yield 81.8%.

The 2-(E)-butenedioate salt (1/1) melts at 104°–109° C.

Analysis for the Formula $C_{29}H_{41}ClN_2O_5$ (533.1): Calculated: C %=65.33; H %=7.75; N %=5.26; Cl %=6.66; found: C %=65.29; H %=7.92; N %=5.22; Cl %=6.65.

U.V.: $\lambda_{max}$=323 nm ($\epsilon$=53985).

EXAMPLE 20

5,5-Dimethyl-3-(E)-[(4'-chloro-phenyl)-vinyl]-1-(E)-(4''-phenyl-methyl-1'''-piperazinyl-propoxyimino)-2-cyclohexene One proceeds in an analogous manner to Example 1 except that 26.4 g (0.1 mole) of 5,5-dimethyl-3-(E)-[(4'-chloro-phenyl)-vinyl]-2-cyclohexene-1-one-(E)-oxime and 27.8 g (0.11 mole) of 1-(4'-phenyl-methyl-1'-piperazinyl)-3-chloro-propane are used as starting material. Thus 48.0 g of the desired compound are obtained, yield 97.6%.

The 2-(E)-butenedioate salt (½) melts at 218°–219° C.
Analysis for the Formula $C_{38}H_{46}ClN_3O_9$ (724.2): Calculated: C %=63.02; H %=6.40; N %=5.80; Cl %=4.90; found: C %=63.10; H %=6.62; N %=5.71; Cl %=4.90.

U.V.: $\lambda_{max}=324$ nm ($\epsilon=52501$).

EXAMPLE 21

5,5-Dimethyl-3-(E)-phenyl-vinyl-1-(E)-[(4''-phenyl-methyl)-piperazinyl]-propoxyimino-2-cyclohexene One proceeds in an analogous manner to Example 1 except that 1-dimethylamino-3-chloro-propane is replaced by 27.8 g (0.11 mole) of 1-(4'-phenyl-methyl-1'-piperazinyl)-3-chloro-propane. Thus 43.3 g of the desired compound are obtained, yield 94.7%.

The 2-(E)-butenedioate salt (½) melts at 210°–212° C.

Analysis for the Formula $C_{38}H_{47}N_3O_9$ (689.8): Calculated: C %=66.16; H %=6.87; N %=6.10; found: C %=66.04; H %=6.91; N %=5.97.

U.V.: $\lambda_{max}=319$ nm ($\epsilon=50887$).

EXAMPLE 22

D,L-5,5-Dimethyl-3-(E)-phenyl-vinyl-1-(E)-[(2'-dimethylamino-2'-methyl)-ethoxyimino]-2-cyclohexene One proceeds in an analogous manner to Example 3 except that 1-dimethylamino-2-chloro-ethane is replaced by 13.3 g (0.11 mole) of D,L-2-dimethylamino-2-methyl-1-chloro-ethane. Thus 26.3 g of the desired compound are obtained, yield 80.5%.

The 2-(E)-butenedioate (1/1) salt melts at 142°–144° C.

Analysis for the Formula $C_{25}H_{34}N_2O_5$ (442.5): Calculated: C %=67.85; H %=7.75; N %=6.33; found: C %=67.82; H %=7.81; N %=6.30.

U.V.: $\lambda_{max}=318$ nm ($\epsilon=47946$).

EXAMPLE 23

5,5-Dimethyl-3-(E)-[(4'-methoxy-phenyl)-vinyl]-1-(E)-(2''-diethylamino-ethoxyimino)-2-cyclohexene One proceeds in an analogous manner to Example 3 except that 27.1 g (0.1 mole) of 5,5-dimethyl-3-(E)-[(4'-methoxy-phenyl)-vinyl]-2-cyclohexene-1-one-(E)-oxime and 14.91 g (0.11 mole) of 1-diethylamino-2-chloro-ethane are used as starting material. Thus 32.5 g of the desired compound are obtained, yield 87.7%.

The 2-(E)-butenedioate salt (1/1) melts at 138°–141° C.

Analysis for the formula $C_{27}H_{38}N_2O_6$ (486.6): Calculated: C%=66.64; H%=7.87; N%=5.76; found: C%=66.75; H%=7.75; N%=5.84.

U. V.: $\lambda_{max}1=331$ nm ($\epsilon=38142$), $\lambda_{max}2=243$ nm ($\epsilon=12940$).

EXAMPLE 24

5,5-Dimethyl-3-(E)-[(4'-chloro-phenyl)-vinyl]-1-(E)-(N-morpholino-propoxyimino)-2-cyclohexane One proceeds in an analogous manner to Example 3 except that 27.5 g (0.1 mole) of 5,5-dimethyl-3-(E)-[(4'-chloro-phenyl)-vinyl]-2-cyclohexene-1-one-(E)-oxime and 18.01 g (0.11 mole) of 1-chloro-3-morpholino-propane are used as starting material. Thus 38.28 g of the desired compound are obtained, yield 95%.

The 2-(E)-butenedioate salt (1/1) melts at 186°–191° C.

Analysis for the formula $C_{27}H_{35}ClH_2O_5$ (519.02); Calculated: C%=62.47; H%=6.79; Cl%=6.83; N%=5.39; found: C%=62.51; H%=6.63; Cl%=6.76; N%=5.35.

U. V.: $\lambda_{max}1=327$ nm ($\epsilon=47821$), $\lambda_{max}2=340$ nm ($\epsilon=37664$).

EXAMPLE 25

D,L-5,5-Dimethyl-3-(E)-[(4'-methoxy-phenyl)-vinyl]-1-(E)-(2''-methyl-3''-dimethylamino-propoxyimino)-2-cyclohexane One proceeds in an analogous manner to Example 3 except that 27.1 g (0.1 mole) of 5,5-dimethyl-3-(E)-[(4'-methoxy-phenyl)-vinyl]-2-cyclohexene-1-one-(E)-oxime and 14.9 g (0.11 mole) of 1-dimethylamino/2-methyl-3-chloro-propane are used as starting material. Thus 30.46 g of the desired compound are obtained, yield 82.2%.

The 2-(E)-butenedioate salt (1/1) melts at 160°–167° C.

Analysis for the Formula $C_{27}H_{38}N_2O_6$ (486.6); Calculated: C%=66.64; H%=7.87; N%=5.76; found: C%=66.56; H%=7.86; N%=5.77.

U. V.: $\lambda_{max}1=330$ nm ($\epsilon=42345$), $\lambda_{max}2=244$ nm ($\epsilon=12199$).

EXAMPLE 26

5,5-Dimethyl-3-(E)-[(2'-chloro-phenyl)-vinyl]-1-(E)-(N-piperdinyl-ethoxyimino)-2-cyclohexene One proceeds in an analogous manner to Example 3 except that 27.5 g (0.1 mole) of 5,5-dimethyl-3-(E)-[(2'-chloro-phenyl)-vinyl]-2-cyclohexene-1-one-(E)-oxime and 14.3 g (0.11 mole) of 1-chloro-2-piperidinyl-ethane are used as starting material. Thus 31 g of the desired compound are obtained, yield 80.3%.

The 2-(E)-butenedioate salt (1/1) melts at 147°–149° C.

Analysis for the formula $C_{27}H_{35}ClN_2O_5$ (503.02); Calculated: C%=64.46; H%=7.01; Cl%=7.04; N%=5.57; found: C%=64.55; H%=6.97; Cl%=7.06; N%=5.55.

U. V.: $\lambda_{max}1=235$ nm ($\epsilon=12600$), $\lambda_{max}2=322$ nm ($\epsilon=41487$).

EXAMPLE 27

5,5-Dimethyl-3-(E)-[(4'-chloro-phenyl)-vinyl]-1-(E)-(N-morpholino-ethoxyimino)-2-cyclohexene One proceeds in an analogous manner to Example 3 except that 27.5 g (0.1 mole) of 5,5-dimethyl-3-(E)-[(4'-chloro-phenyl)-vinyl]-2-cyclohexene-1-one-(E)-oxime and 16.46 g (0.11 mole) of 1-chloro-2-morpholino-ethane are used as starting material. Thus 36.56 g of the desired compound are obtained, yield 94%.

The 2-(E)-butenedioate salt (1/1) melts at 154°–157° C.

Analysis for the Formula $C_{26}H_{33}ClN_2O_6$ (504.99); Calculated: C%=61.83; H%=6.58; Cl%=7.01; N%=5.54; found: C%=61.81; H%=6.53; Cl%=6.95; N%=5.59.

U. V.: $\lambda_{max}1=327$ nm ($\epsilon=48132$), $\lambda_{max}2=340$ nm ($\epsilon=36921$).

EXAMPLE 28

5,5-Dimethyl-3-(E)-[(3'-chloro-phenyl)-vinyl]-1-(E)-(N-morpholino-ethoxyimino)-2-cyclohexene One proceeds in an analogous manner to Example 3 except that 27.5 g (0.1 mole) of 5,5-dimethyl-3-(E)-[(3'-chloro-phenyl)-vinyl]-2-cyclohexene-1-one-(E)-oxime and 16.4 g (0.11 mole) of 1-chloro-2-morpholino-ethane are used as starting material. Thus 33.91 g of the desired compound are obtained, yield 87.2%.

The 2-(E)-butenedioate salt (1/1) melts at 136°–138° C.

Analysis for the Formula $C_{26}H_{33}ClN_2O_6$ (504.99); Calculated: C%=61.83; H%=6.58; Cl%=7.01; N%=5.54; found: C%=61.62; H%=6.59; Cl%=6.96; N%=5.49.

U. V.: $\lambda_{max}1=324$ nm ($\epsilon=43152$), $\lambda_{max}2=337$ nm ($\epsilon=33209$).

EXAMPLE 29

5,5-Dimethyl-3-(E)-[(3'-methoxy-phenyl)-vinyl]-1-(E)-(N-morpholino-ethoxyimino)-2-cyclohexene One proceeds in an analogous manner to Example 3 except that 27.1 g (0.1 mole) of 5,5-dimethyl-3-(E)-[(3'-methoxy-phenyl)-vinyl]-2-cyclohexene-1-one-(E)-oxime and 16.46 g (0.11 mole) of 1-chloro-2-morpholino-ethane are used as starting material. Thus 31.8 g of the desired compound are obtained, yield 82.7%.

The 2-(E)-butenedioate salt (1/1) melts at 123°–125° C.

Analysis for the Formula $C_{27}H_{36}N_2O_7$; Calculated: C% 64.77; H%=7.24; N%=5.59; found: C% 64.52; H%=7.17; N%=5.56.

U. V.: $\lambda_{max}=327$ nm ($\epsilon=42260$).

EXAMPLE 30

5,5-Dimethyl-3-(E)-[(3'-methoxy-phenyl)-vinyl]-1-(E)-(N-morpholino-propoxyimino)-2-cyclohexene One proceeds in an analogous manner to Example 3 except that 27.1 g (0.1 mole) of 5,5-dimethyl-3-(E)-[(3'-methoxy-phenyl)-vinyl]-2-cyclohexene-1-one-(E)-oxime and 18.01 g (0.11 mole) of 1-chloro-3-morpholino-propane are used as starting material. Thus 35.78 g of the desired compound are obtained, yield 89.8%.

The 2-(E)-butenedioate salt (1/1) melts at 125°–130° C.

Analysis for the Formula $C_{28}H_{32}N_2O_7$ (514.6); Calculated: C%=65.34; H%=7.14; N%=5.44; found: C%=66.74; H%=7.75; N%=5.47.

U. V.: $\lambda_{max}=327$ nm ($\epsilon=41736$).

EXAMPLE 31

5,5-Dimethyl-3-(E)-[(4'-chloro-phenyl)-vinyl]-1-(E)-(2"-diethylamino-ethoxyimino)-2-cyclohexene One proceeds in an analogous manner to Example 3 except that 27.5 g (0.1 mole) of 5,5-dimethyl-3-(E)-[(4'-chloro-phenyl)-vinyl]-2-cyclohexene-1-one-(E)-oxime and 14.91 g (0.11 mole) of 1-diethylamino-2-chloro-ethane are used as starting material. Thus 33.45 g of the desired compound are obtained. Yield 89.2%.

The 2-(E)-butenedioate salt (1/1) melts at 134°–137° C.

Analysis for the Formula $C_{26}H_{35}ClN_2O_5$ (491.0); Calculated: C%=63.59; H%=7.19; Cl%=7.22; N%=5.7; found: C%=63.50; H%=7.13; Cl%=7.20; N%=5.65.

U. V.: $\lambda_{max}1=323$ nm ($\epsilon=51805$), $\lambda_{max}2=239$ nm ($\epsilon=13375$).

EXAMPLE 32

5,5-Dimethyl-3-(E)-[(2'-methoxy-phenyl)-vinyl]-1-(E)-(2"-diisopropylamino-ethoxyimino)-2-cyclohexene One proceeds in an analogous manner to Example 3 except that 27.1 g (0.1 mole) of 5,5-dimethyl-3-(E)-[(2'-methoxy-phenyl)-vinyl]-2-cyclohexene-1-one-(E)-oxime and 18.8 g (0.11 mole) of 1-diisopropylamino-2-chloro-ethane are used as starting material. Thus 34.64 g of the desired compound are obtained, yield 87%.

The 2-(E)-butenedioate salt (1/1) melts at 131°–133° C.

Analysis for the Formula $C_{29}H_{42}N_2O_6$ (514.2); Calculated: C%=67.71; H%=8.17; N%=5.44; found: C%=67.57; H%=8.22; N%=5.56.

U. V.: $\lambda_{max}1=336$ nm ($\epsilon=30953$), $\lambda_{max}2=240$ nm ($\epsilon=11878$).

EXAMPLE 33

5,5-Dimethyl-3-(E)-[(2'-methoxy-phenyl)-vinyl]-1-(E)-(N-piperidinyl-ethoxyimino)-cyclohexene One proceeds in an analogous manner to Example 3 except that 27.1 g (0.1 mole) of 5,5-dimethyl-3-(E)-[(2'-methoxy-phenyl)-vinyl]-2-cyclohexene-1-one-(E)-oxime and 14.3 g (0.11 mole) of 1-chloro-2-piperidinyl-ethane are used as starting material. Thus 34.78 g of the desired compound are obtained, yield 91%.

The 2-(E)-butenedioate salt (1/1) melts at 146°–148° C.

Analysis for the Formula $C_{28}H_{38}N_2O_6$ (498.6); Calculated: C%=67.44; H%=7.68; N%=5.61; found: C%=67.29; H%=7.77; N%=5.59.

U. V.: $\lambda_{max}=338$ nm ($\epsilon=37914$).

EXAMPLE 34

5,5-Dimethyl-3-(E)-[(3'-chloro-phenyl)-vinyl]-1-(E)-(N-morpholino-propoxyimino)-2-cyclohexene One proceeds in an analogous manner to Example 3 except that 27.5 g (0.1 mole) of 5,5-dimethyl-3-(E)-[(3'-chloro-phenyl)-vinyl]-2-cyclohexane-1-one-(E)-oxime and 18.81 g (0.1 mole) of 1-chloro-3-morpholino-propane are used as starting material. Thus 37.56 g of the desired compound are obtained, yield 93.4%.

The 2-(E)-butenedioate salt (1/1) melts at 141°–145° C.

Analysis for the Formula $C_{27}H_{35}ClN_2O_6$ (519.02); Calculated: C%=62.47; H%=6.79; Cl%=6.83; N%=5.39; found: C%=62.61; H%=6.71; Cl%=6.85; N%=5.33.

U. V.: $\lambda_{max}1=320$ nm ($\epsilon=43529$), $\lambda_{max}2=239$ nm ($\epsilon=12868$).

EXAMPLE 35

Injectable Compositions Having an Active Ingredient Content of 25 mg

One ampoule is of the following composition:

| Component | Amount |
| --- | --- |
| Active Ingredient | 25.0 mg |
| Twice distilled water | 5 ml |

EXAMPLE 36

Tablets Having an Active Ingredient Content of 25 mg

Tablets having the following composition are prepared:

| Component | Amount, mg |
| --- | --- |
| Active ingredient | 25.0 |
| Maize starch | 97.0 |

| Component | Amount, mg |
|---|---|
| Polivinyl pyrrolidone | 175.0 |
| Magnesium stearate | 3.0 |
| Total weight | 300.0 |

A mixture of the active ingredient and maize starch is subjected to wet granulation wiht a 10-15% aqueous polyvinyl pyrrolidone solution. The granules are dried, admixed with the magnesium stearate and pressed to tablets.

EXAMPLE 37

Dragées Having an Active Ingredient Content of 25 mg

Dragée cores having the following composition are prepared:

| Component | Amount, mg |
|---|---|
| Active ingredient | 25.0 |
| Maize starch | 245.0 |
| Gelatine | 8.0 |
| Talc | 18.0 |
| Magnesium stearate | 4.0 |
| Total weight | 300.0 |

A mixture of the active ingredient and maize starch is wetted with a 10% aqueous gelatine solution, granulated by passing through a sieve and the granules are dried at 40°-45° C. The dry granules are passed again through a sieve, homogenized with the talc and the magnesium stearate and pressed to dragée cores weighing 300.0 mg.

The dragee cores are coated with a layer consisting of sugar and talc in a known manner. The dragees thus obtained are dyed with an atoxical foodstuff-dye to the desired colour and polished with bee-wax.

EXAMPLE 38

Dragées Having an Active Ingredient Content of 25 mg

Dragee cores having the following composition are prepared

| Component | Amount, mg |
|---|---|
| Active ingredient | 50.0 |
| Lactose | 97.0 |
| Polivinyl pyrrolidone | 2.0 |
| Magnesium stearate | 1.0 |
| Total weight | 150.0 |

The preparation, coating and polishing of the dragee cores is carried out as described in Example 37.

EXAMPLE 39

Gelatine Capsules Having an Active Ingredient Content of 100 mg

Gelatine capsules having the following composition

| Component | Amount, mg |
|---|---|
| Active ingredient | 100.0 |
| Maize starch | 190.0 |
| Aerosil | 6.0 |
| Magnesium stearate | 4.0 |
| Total weight | 300.0 |

The above components are homogenized and the mixture is filled into gelatine capsules of suitable size.

What is claimed is:

1. A compound of formula I Formula I

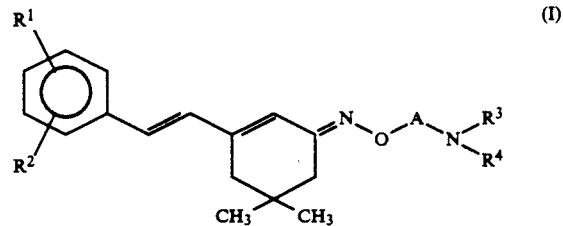

wherein
A stands for a $C_{2-4}$ straight or branched chain alkylene group;
$R^1$ and $R^2$ may be same or different and each stands for hydrogen, halogen, lower alkyl or lower alkoxy; or
$R^1$ and $R^2$ together form a methylenedioxy group;
$R^3$ and $R^4$ may be the same or different and each stands for $C_{1-5}$ alkyl or $C_{3-6}$ cycloalkyl or
$R^3$ and $R^4$ together with the nitrogen atom to which they are attached, form a 4-7 membered ring which may contain as additional ring member an oxygen or sulfur atom or a further nitrogen atom and the latter nitrogen atom may optionally bear a $C_{1-3}$ alkyl or benzyl substitutent
and pharmaceutically acceptable acid addition salts and quaternary ammonium salts thereof.

2. A compound according to claim 1, wherein A stands for ethylene, trimethylene or 2-methyl-1-trimethylene.

3. A compound according to claim 1, wherein A stands for ethylene, trimethylene or 2-methyl-trimethylene.

4. A compound according to claim 1, wherein $R^3$ and $R^4$ may be the same or different and each stands for methyl or ethyl.

5. A compound according to claim 1, wherein $R^3$ and $R^4$ together with the adjacent nitrogen atom form a piperazinyl, N-methyl-piperazinyl, N-benzyl-piperazinyl, morpholino, piperidino or pyrrolidino ring.

6. A pharmaceutical composition having tranquillant-sedative, antidepressant, antiepileptic, antiparkinson, analgesic, local anaesthetic, gastric acid secretion inhibiting and antianginal activity which comprises: an inert pharmaceutical carrier and an effective amount of a compound of the formula I as defined in claim 1.

7. A method of administering a tranquillant-sedative, anti-depressant, anti-epileptic, anti-parkinson, analgesic, local anaesthetic, gastric acid secretion inhibiting and anti-anginal treatment to a patient in need thereof which comprises administering to said patient an effective amount of a compound of the formula I as defined in claim 1.

8. The compound of claim 1 which is 5,5-dimethyl-3-(E)-[(4'-chloro-phenyl)-vinyl]-1-(E)-(4''-phenyl-methyl-1''-piperazinyl-propoxyimino)-2-cyclohexene.

9. The compound of claim 1 which is 5,5-dimethyl-3-(E)-[(4'-methoxy-phenyl)-vinyl]-1-(E)-(2''-diethylamino-ethoxyimino)-2-cyclohexene.

10. The compound of claim 1 which is 5,5-dimethyl-3-(E)-[(4'-chloro-phenyl)-vinyl]-1-(E)-(N-morpholino-propoxyimino)-2-cyclohexene.

11. The compound of claim 1 which is D,L-5,5-dimethyl-3-(E)-[(4'-methoxy-phenyl)-vinyl]-1-(E)-(2''- methyl-3"-dimethylamino-propoxyimino)-2-cyclohexene.

12. The compound of claim 1 which is 5,5-dimethyl-3-(E)-[(2'-chloro-phenyl)-vinyl]-1-(E)-(N-piperidinyl-ethoxyimino)-2-cyclohexene.

13. The compound of claim 1 which is 5,5-dimethyl-3-(E)-[(3'-chloro-phenyl)-vinyl]-1-(E)-(N-morpholino-ethoxyimino)-2-cyclohexene.

14. The compound of claim 1 which is 5,5-dimethyl-3-(E)-[(3'-methoxy-phenyl)-vinyl]-1-(E)-(N-morpholino-ethoxyimino)-2-cyclohexene.

15. The compound of claim 1 which is 5,5-dimethyl-3-(E)-[(3'-methoxy-phenyl)-vinyl]-1-(E)-(N-morpholino-propoxyimino)-2-cyclohexene.

16. The compound of claim 1 which is 5,5dimethyl-3-(E)-[(2'-methoxy-phenyl)-vinyl]-1-(E)-(N-poperidinyl-ethoxyimino)-cyclohexene.

17. The compound of claim 1 which is 5,5-dimethyl-3-(E)-[(3'-chloro-phenyl)-vinyl]-1-(E)-(N-morphoolino-propoxyimino)-2-cyclohexene.

* * * * *